United States Patent
Keller et al.

(10) Patent No.: US 10,426,613 B2
(45) Date of Patent: Oct. 1, 2019

(54) DELIVERY CATHETER AND CATHETER ARRANGEMENT

(71) Applicant: BIOTRONIK AG, Buelach (CH)

(72) Inventors: Mark Keller, Aarau (CH); Markus Hepke, Zurich (CH); Peter Maspoli, Buelach (CH)

(73) Assignee: BIOTRONIK AG, Buelach (CH)

( * ) Notice: Subject to any disclaimer, the term of this patent is extended or adjusted under 35 U.S.C. 154(b) by 252 days.

(21) Appl. No.: 15/440,931

(22) Filed: Feb. 23, 2017

(65) Prior Publication Data
US 2017/0252158 A1 Sep. 7, 2017

(30) Foreign Application Priority Data
Mar. 3, 2016 (EP) .................................... 16158376

(51) Int. Cl.
*A61F 2/962* (2013.01)
*A61F 2/24* (2006.01)
(Continued)

(52) U.S. Cl.
CPC ........ *A61F 2/2427* (2013.01); *A61B 17/0057* (2013.01); *A61B 17/12122* (2013.01);
(Continued)

(58) Field of Classification Search
CPC .......... A61F 2/2427; A61F 2/962; A61F 2/01; A61F 2/2436; A61F 2/966; A61F 2002/011; A61F 2230/0067; A61F 2250/0018; A61F 2250/0029; A61F 2250/0039; A61B 17/3468; A61B 17/12122; A61B 17/0057;
(Continued)

(56) References Cited

U.S. PATENT DOCUMENTS

| 6,395,017 B1 * | 5/2002 | Dwyer | A61F 2/962 |
| | | | 623/1.11 |
| 8,221,390 B2 * | 7/2012 | Pal | A61F 2/95 |
| | | | 604/535 |

(Continued)

FOREIGN PATENT DOCUMENTS

WO 2015031024 A1 3/2015

OTHER PUBLICATIONS

Geuer, Melanie, "European Search Report", European Patent Application No. EP 16 15 8376, dated Aug. 4, 2016, 5 pages.
(Continued)

*Primary Examiner* — Julian W Woo
(74) *Attorney, Agent, or Firm* — Greer, Burns & Crain, Ltd.; Steven P. Fallon

(57) ABSTRACT

A delivery catheter for implanting a self-expanding implant such as a cardiovascular implant. An outer catheter shaft is formed as an implant capsule for encasing the implant during delivery. A flexible distal support element having a substantially truncated cone-shaped portion, which tapers in the proximal direction, is attached, directly proximally of the implant, in a fixed position to a first, inner catheter shaft, and/or a flexible proximal support element having a substantially truncated cone-shaped portion, which tapers in the proximal direction, is inserted at the proximal end of the implant capsule into the second, outer catheter shaft in a fixed position.

26 Claims, 2 Drawing Sheets

(51) Int. Cl.
| | |
|---|---|
| *A61B 17/34* | (2006.01) |
| *A61B 17/00* | (2006.01) |
| *A61B 17/12* | (2006.01) |
| *A61F 2/01* | (2006.01) |
| *A61F 2/966* | (2013.01) |
| *A61M 25/00* | (2006.01) |

(52) U.S. Cl.
CPC .......... *A61B 17/3468* (2013.01); *A61F 2/01* (2013.01); *A61F 2/2436* (2013.01); *A61F 2/962* (2013.01); *A61F 2/966* (2013.01); *A61B 2017/00623* (2013.01); *A61B 2017/1205* (2013.01); *A61B 2017/12054* (2013.01); *A61B 2017/347* (2013.01); *A61F 2002/011* (2013.01); *A61F 2230/0067* (2013.01); *A61F 2250/0018* (2013.01); *A61F 2250/0029* (2013.01); *A61F 2250/0039* (2013.01); *A61M 25/0013* (2013.01); *A61M 2025/0098* (2013.01)

(58) Field of Classification Search
CPC .... A61B 2017/12054; A61B 2017/347; A61B 2017/1205; A61B 2017/00623; A61M 25/0013; A61M 2025/0098

USPC .......................... 623/1.11, 1.12, 2.11
See application file for complete search history.

(56) References Cited

U.S. PATENT DOCUMENTS

| | | | |
|---|---|---|---|
| 8,273,116 B2* | 9/2012 | Licata ................ | A61F 2/95 623/1.11 |
| 8,562,673 B2 | 10/2013 | Yueng et al. | |
| 8,663,302 B2* | 3/2014 | Schmitt ............... | A61F 2/95 623/1.11 |
| 8,728,116 B1* | 5/2014 | Janardhan ........... | A61F 2/01 606/200 |
| 8,986,362 B2* | 3/2015 | Snow .................. | A61F 2/95 606/108 |
| 9,398,902 B2* | 7/2016 | Paul, Jr. ............. | A61B 17/0057 |
| 9,439,795 B2* | 9/2016 | Wang .................. | A61F 2/2436 |
| 2013/0110223 A1 | 5/2013 | Munsinger et al. | |
| 2014/0277574 A1 | 9/2014 | Liljegren et al. | |

OTHER PUBLICATIONS

Melanie Geuer, European Search Report for Application No. 17158339.6, dated Mar. 21, 2017.

* cited by examiner

DELIVERY CATHETER AND CATHETER ARRANGEMENT

PRIORITY CLAIM

This application claims priority under 35 U.S.C. § 119 and all applicable statutes and treaties from prior European Application EP 16158376.0, filed Mar. 3, 2016.

FIELD OF THE INVENTION

A field of the invention is delivery catheters for self-expanding implants. Delivery catheters of the invention can be used to deliver self-expanding implants such as cardiovascular implants, including prosthetic heart valves. Additional example self-expanding implants include stent systems for closing the left atrial appendage, stent systems for closing patent foramen ovale, stent systems for closing any kind of arterial septal defects (occluders) or self-expanding filter or protector systems.

BACKGROUND

Minimally invasive surgical interventions have gained steadily in importance for years and are indispensable for example for the treatment of stenoses. Recently, they have also been used increasingly in the implantation of artificial heart valves. Suitable delivery catheters are known in a very wide range of designs and are the subject of on-going further development. In recent years, the development has focused particular attention on catheters which not only permit the placement, but also the removal or a repositioning (when necessary) of cardiovascular implants.

Delivery catheters of this type consist fundamentally of a first, inner catheter shaft, at the distal end of which there is arranged the implant. The implant and the first, inner catheter shaft are surrounded by a second, outer catheter shaft. The distal region of the second outer catheter shaft, which surrounds the implant, is often referred to as an implant capsule, or occasionally as a catheter sleeve. Here, the implant capsule can consist of the same material as the second outer catheter shaft or of another material connected to the second outer catheter shaft. Here, the position reference "proximal" denotes a part of the delivery catheter disposed closer to the user, and "distal" accordingly denotes a part of the delivery catheter disposed further away from the user.

The implants (in particular the heart valve stent) are often made of a shape-memory material. In these cases, the implants are held in their compressed form by the catheter sleeve surrounding them as they are delivered to the site of implantation. Displacement of the catheter sleeve, for example proximally, gradually releases the implant as the sleeve is withdrawn and permits the implant to expand.

Recently, solutions have been proposed which were supposed to permit a return (resheathing or recapturing) of an already partially released implant into the delivery catheter, i.e. especially into the implant capsule. Such resheathing is of great advantage to surgeons because the resheathing permits corrections during the delivery process and thus helps the implantation process to be concluded with the best-possible results. Especially in cases in which the implant is released by retracting the catheter sleeve proximally, relatively high reaction forces or high local stress concentrations occur as the heart valve stent is returned into the implant capsule or, more specifically, as the distal catheter end is drawn back over the stent. These forces and stresses lead to complex problems. See, e.g. Yeung et al., U.S. Pat. No. 8,562,673, entitled Stented transcatheter prosthetic heart valve delivery system and method. The '673 patent uses a tubular shape memory capsule in the form of a cut tube with longitudinal splines/wires that provide reinforcement. The capsule includes a distal zone that transitions to a flared state and imparts a collapsing force onto a prosthesis when the capsule is moved back over the prosthesis, causing the prosthesis to radially collapse and become recaptured within the delivery capsule. This process places high local stresses on a heart valve prosthesis at the point where the collapsing force is applied by the transition region.

SUMMARY OF THE INVENTION

A preferred embodiment provides delivery catheter for implanting a self-expanding implant. The catheter includes a first, inner catheter shaft arranged inside at least one second, outer catheter shaft. The implant is arranged in the distal region of the delivery catheter on the first, inner catheter shaft, and a distal portion the second, outer catheter shaft is formed as an implant capsule for encasing the implant during the insertion process. A flexible distal support element having a substantially truncated cone-shaped portion, which tapers in the proximal direction, is attached, directly proximally of the implant, in a fixed position to the first, inner catheter shaft, and/or a flexible proximal support element having a substantially truncated cone-shaped portion, which tapers in the proximal direction, is inserted at the proximal end of the implant capsule into the second, outer catheter shaft in a fixed position.

BRIEF DESCRIPTION OF THE DRAWINGS

Advantages and expedient features of the invention will also become clear from the following description of an exemplary embodiment provided with reference to the figures, in which.

DETAILED DESCRIPTION OF THE PREFERRED EMBODIMENTS

Figure 1:
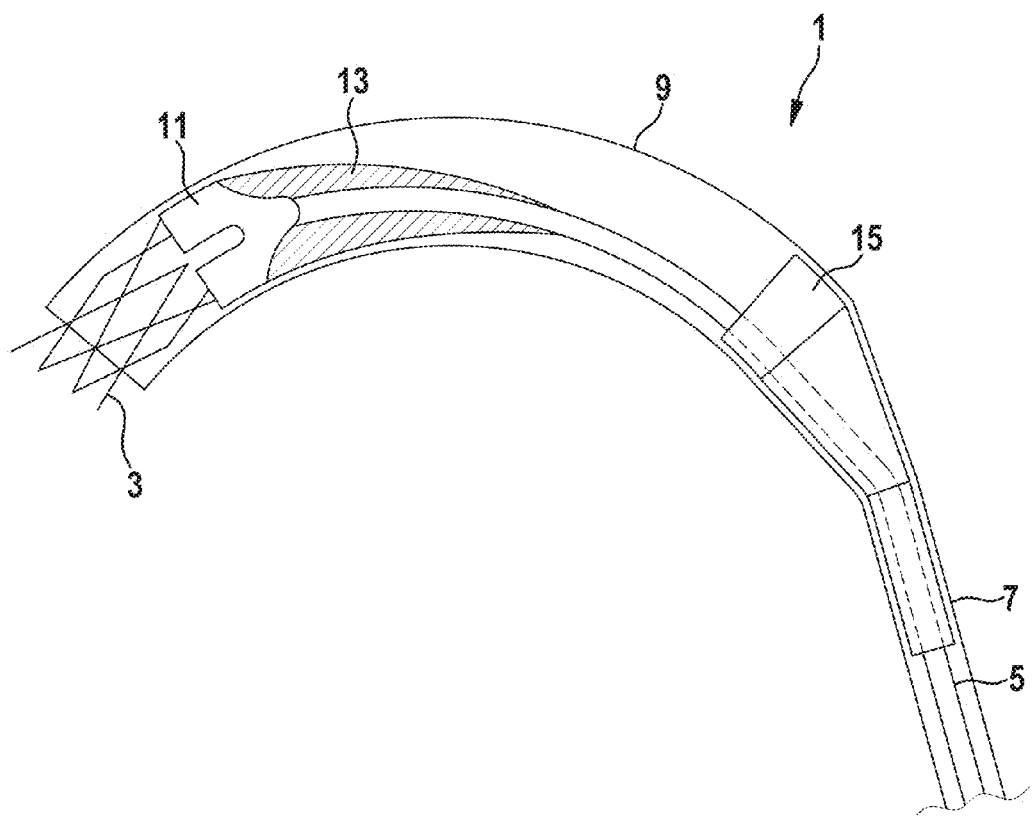
FIG. 1 shows a schematic longitudinal sectional illustration of the distal portion of a delivery catheter in the state of partial resheathing.

The present inventors have determined by carrying out practical tests on known systems, there may be a functional failure of the implant capsule as it is guided back over the implant, more specifically in particular there may be a formation of kinks on the implant capsule which hinder the resheathing or make it practically or completely impossible. This is attributed to high local forces being applied to the implant during resheathing. Preferred delivery catheters of the invention reduce localized forces to implants during resheathing compared to prior delivery catheters known to the invention. Preferred embodiments provide an improved delivery catheter with which in particular a formation of kinks in the region of the implant capsule is largely prevented, hereby permitting reliable and easy resheathing.

The invention relates to a delivery catheter for implanting a cardiovascular implant, in particular a prosthetic heart valve, said delivery catheter comprising a first, inner catheter shaft, which is arranged inside at least one second, outer catheter shaft, wherein the implant is arranged in the distal region of the delivery catheter on the first, inner catheter shaft, and wherein a portion close to the distal end of the second, outer catheter shaft is formed as an implant capsule for encasing the implant during the insertion process. The invention also relates to a catheter arrangement formed with said delivery catheter.

The invention relates to a delivery catheter for implanting a self-expanding implant. Self-expanding implants of this type are in particular stents, prosthetic heart valves, prosthetic venous valves, stent systems for closing the left atrial appendage, stent systems for closing patent foramen ovale, stent systems for closing any kind of arterial septal defects (occluders) or self-expanding filter or protector systems. The invention is suitable in particular for delivery catheters for prosthetic heart valves which have a self-expanding main frame (heart valve stent) and a valve arrangement secured thereto, for example made of biological tissue. Preferred embodiments are therefore illustrated with the example of a prosthetic heart valve of this type as in particular used as aortic valve replacement.

The present invention includes the concept of providing a reinforcement in the region of the implant capsule, which reinforcement acts dynamically to a certain extent and which, in contrast to previously proposed solutions, does not simply constitute an overall reinforcement of the capsule by increasing the wall thickness or by providing a particularly thick inner catheter shaft. According to the findings of the inventors, these earlier proposed solutions specifically have disadvantages in respect of the flexibility of the catheter, in particular in the case of complex implant designs, such as prosthetic heart valves. The same is true for self-expanding implants which are released into smaller, curved vessels.

In accordance with the invention, it is provided that a flexible distal support element having a substantially truncated cone-shaped portion, which tapers in the proximal direction, is attached, directly proximally of the implant, in a fixed position to the first, inner catheter shaft, and/or that a flexible proximal support element having a substantially truncated cone-shaped portion, which tapers in the proximal direction, is inserted at the proximal end of the implant capsule into the second, outer catheter shaft in a fixed position. The cones, which are provided hereby in the region of the implant capsule and which are each movable in relation to one of the catheter elements displaceable relative to one another, largely suppress the tendency towards kink formation in the event of bending moments and axial compressive forces occurring together, as are observed in the case of resheathing. The previously observed kinking, collapse, and therefore failure of the distal outer catheter sleeve or implant capsule can thus be largely prevented.

A truncated cone-shaped portion is understood here to mean any substantially rotationally symmetrical truncated cone-like shape which changes from a small cross-section to a large cross-section. This includes truncated cones in the strict mathematical sense and also truncated cones where the connection between the different cross-sections deviates from a straight line (in contrast to a mathematical cone). In particular, truncated cones of which the outer sides are slightly concave or convex when cut along the longitudinal axis can also be included.

Here, the term "directly proximally of the implant" is understood to mean an arrangement in which the support elements has no distance or only a very short distance from the implant. In the case of delivery catheters where the implant is connected at its proximal end to the first inner shaft by means of a holding element (also known as prosthesis connector) or otherwise, the support element would be disposed directly proximally beside a holding element of this type.

The proximal support element, in addition to its support function, also connects the second outer shaft to the actual implant capsule and thus forms a transition from the second outer shaft to the actual implant capsule.

In one embodiment of the invention the proximal support element includes a cylindrical distal portion, of which the diameter is adapted to the inner diameter of the implant capsule and the outer diameter of the crimped implant, a cylindrical proximal portion, of which the outer diameter is adapted to the inner diameter of the second, outer catheter shaft, and a substantially truncated cone-shaped middle portion, which forms a continuous transition between the distal and proximal cylindrical portion. More specifically, it can be formed as an injection-moulded part or turned part, but also as appropriate can be produced by partial reaming from a tube piece. Production by means of thermoforming (deep-drawing) or blow moulding is likewise conceivable. Metals, such as steel or Nitinol, or plastics are expedient as material for the support element.

In a further embodiment the proximal support element, in particular at least in the middle portion, has a multiplicity of incisions, which provide the flexibility of the support element. The support element is in particular configured such that the incisions extend tangentially over a part of, preferably over the majority of the periphery of the support element. In this embodiment of the invention the proximal support element is embodied as a cone formed from a slotted metal tube ("laser cut metal tube").

The first proximal support element preferably forms the connection between the second outer catheter shaft and the implant capsule, or the proximal support element is inserted within the implant capsule at the proximal end thereof and is connected thereto. In any case, the proximal support element is formed in such a way that the relative movability between the second outer shaft or implant capsule and the first inner catheter shaft is ensured, i.e. in such a way that the proximal support element has an appropriate inner lumen corresponding at least to the diameter of the first inner catheter shaft.

In a further embodiment, it is provided that the distal support element has a distal end, of which the outer diameter is adapted to the inner diameter of the implant capsule and the outer diameter of the crimped implant, and a proximal end, of which the inner diameter is adapted to the outer diameter of the first, inner catheter shaft. Furthermore, the distal support element is formed in particular as a solid or non-solid plastics part with an inner lumen of which the diameter is adapted to the inner diameter of the first, inner catheter shaft. Manufacture of the distal support element as a part which is separate from the inner catheter shaft and which is fitted onto the inner catheter shaft and is welded or glued thereto is currently preferred. In principle, however, the distal support element can also be manufactured integrally with the first, inner catheter shaft. The distal support element is preferably an injection-moulded part or turned part and can optionally have a multiplicity of incisions for increasing the flexibility. In principle, the distal support element can be formed as described above for the proximal support element.

In further embodiments of the invention, the implant capsule is increased by the longitudinal extent of the distal support element (if provided) and/or of the proximal support element (if provided) compared to the length based on the length of the crimped implant. Depending on the specific embodiment of the implant on the one hand and of the distal and/or proximal support element on the other hand, such an extension of the implant capsule, however, can also be expendable.

In further embodiments of the invention, the dimensioning of the support element or each support element is selected such that the ratio between length and greatest diameter of the support element is between 2 and 7, preferably between 3 and 5, and particularly preferably between 3.5 and 4.5. Furthermore, in combination with these dimensioning specifications or also independently hereof, the ratio between the length of the distal and/or the proximal support element and the length of the implant capsule is preferably between 0.13 and 0.82, in particular between 0.28 and 0.42.

In a preferred embodiment with an implant capsule having an outer diameter of from 14 French (4.7 mm) to 21 French (7 mm) and a length of from 60 mm to 80 mm, the proximal and/or distal support element have/has a length of from 10 mm to 50 mm, preferably between 20 mm and 25 mm. The greatest diameter of the support element/support elements is then between 4.5 mm and 6.5 mm depending on the used wall thickness of the implant capsule.

Currently, an embodiment of the invention in which both a distal and a proximal support element is provided and both together support a proportion of the length of the implant capsule of at least 0.25 to 0.85, preferably from 0.45 to 0.65, is preferred. This is indeed more complex than the provision of just one support element, but provides the greatest possible security against kink formation and subsequent failure of the implant capsule or outer catheter sleeve.

In embodiments of the invention where both a distal and a proximal support element are used, the two support elements are preferably embodied so as to fit one inside the other. The proximal support element is then preferably embodied as a hollow body. In the delivery state of the catheter, the implant is covered by the implant capsule and is held in its compressed form. In the delivery state, the distal support element is therefore preferably arranged on the inner shaft at least in part within the proximal support element, which forms a transition between the second outer catheter shaft and the implant capsule. In order to prevent a wedging of the distal support element in the proximal support element, a stop is preferably arranged within the proximal support element. Alternatively, the angles of the conical portions of the proximal and distal support element can be different. The two cones therefore do not fit perfectly one inside the other. As another alternative the inner surface of the proximal support element and/or the outer surface of the distal support element is/are structured (e.g. a surface texture, grooves or pimples are provided) to avoid wedging. All three different alternative embodiments to avoid wedging could be combined in any possible way.

In a preferred embodiment of the invention, the delivery catheter is equipped with both support elements, a proximal and a distal support element. The distal support element as well as the proximal support element is preferably a turned part made of stainless steel. Both support elements are preferably laser cut stainless steel cones, which exhibit incisions/cuts extending tangentially over a part of, preferably over the majority of the periphery of the support element. The implant connector (prosthesis holding element) is preferably an integral (the distal) part of the distal support element.

FIG. 1 schematically shows (not to scale), with no consideration of the wall thickness or other structural details, the distal end of a delivery catheter 1 for inserting a prosthetic heart valve 3, which is shown here in the state partially retracted into the distal end of the delivery catheter 1 (partial resheathing). The delivery catheter 1 includes a first, inner catheter shaft 5 and a second, outer catheter shaft 7, and at the distal end of the latter an implant capsule 9 of widened diameter is provided.

An implant connector 11 (prosthesis connector) is attached to the distal part of the first, inner catheter shaft 5, in a manner likewise known per se. The implant connector is connected to the first, inner catheter shaft and has eyelets or cut-outs, in which a corresponding counter piece of the implant engages in order to fix the implant axially on the first inner catheter shaft as long as the implant connector 11 is covered by the implant capsule. The reverse variant is also expedient. The first, inner catheter shaft 5 and the second, outer catheter shaft 7 are displaceable relative to one another in the longitudinal direction of the delivery catheter 1, which permits both a release of the stent of the prosthetic heart valve 3 (which stent is typically manufactured from a shape-memory alloy) and the aforementioned resheathing thereof by manual control on the part of the surgeon from the proximal catheter end (not shown).

A conical distal support element 13 is attached to the inner catheter shaft 5 directly proximally of the implant connector 11, and a proximal support element 15 is attached to the outer catheter shaft 7 at the proximal end of the implant capsule 9. Whereas the distal support element 13 is movable together with the inner catheter shaft 5, the proximal support element 15 is movable together with the outer catheter shaft 7. Each of the two support elements 13, 15 individually, and even better both together, serves/serve to prevent a kinking of the delivery catheter 1 in the region of the implant capsule thereof and to prevent said delivery catheter from being rendered useless as the prosthetic heart valve 3 is returned into the implant capsule 9.

The distal support element 13 is preferably connected to the implant connector 11. The connection can be embodied as a welded, glued, or screwed connection. In principle, any suitable connection of distal support element 13 and implant connector 11 is possible. An embodiment in which the implant connector 11 and distal support element 13 form an integral component is also expedient.

Figure 2:
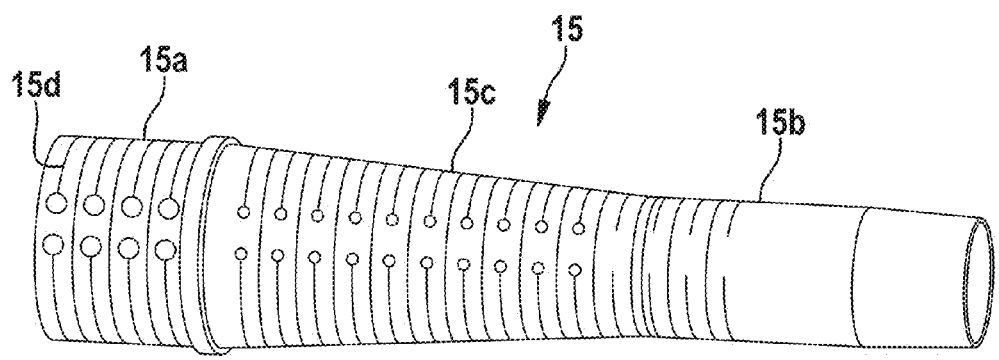
FIG. 2 shows a perspective illustration of an embodiment of the proximal support element of the delivery catheter according to FIG. 1.

FIG. 2 shows an exemplary embodiment of the proximal support element 15, which here includes a first cylindrical portion 15a, a second cylindrical portion 15b of smaller diameter, and a conical portion 15c connecting the two cylindrical portions 15a, 15b to each other. The proximal support element is flexible from the distal end of the cylindrical portion 15b to the distal end of the support element 15 by means of incisions 15d running tangentially over the majority of the circumference.

The distal support element 13 and/or proximal support element 15 can be embodied as cut stainless steel cones. Here, it is expedient to weld the cut stainless steel cones of the support element 13 and/or 15 to the cut stainless steel cores of the first inner or second outer catheter shaft. Here, the cut stainless steel cores or stainless steel cones are advantageously encased on the inside and/or outside by plastic so as to ensure that they slide one inside the other or relative to the vessel wall with less friction. Additionally the plastic encase functions as a seal.

Figure 3:
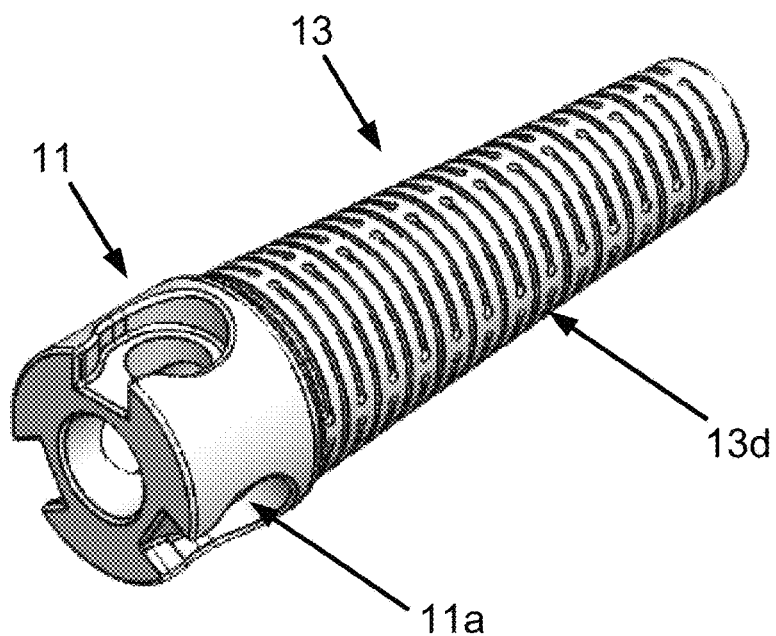
FIG. 3 shows a perspective illustration of an embodiment of the distal support element of the delivery catheter according to FIG. 1.

FIG. 3 shows an exemplary embodiment of the distal support element 13. According to this embodiment, the implant connector 11 is an integral part of the distal support element 13. The distal support element 13 and the implant connector 11 are forming an integral element, which is made of stainless steel. The implant connector 11 includes openings or eyelets 11a suitable for receiving corresponding counter pieces (locking elements) of the implant (not shown). Due to the fit between the openings 11a and the locking elements of the implant the implant is axially fixed on the delivery catheter 1. The distal support element 13 is a laser cut stainless steel cone, where the incisions 13d provide a certain flexibility of the distal support element 13.

The invention claimed is:

1. A delivery catheter for implanting a self-expanding implant, the delivery catheter comprising a first, inner catheter shaft arranged inside at least one second, outer catheter shaft, and an implant connector attached to a distal region of the inner catheter shaft, wherein the implant connector comprises eyelets or cut-outs, wherein the implant is arranged in the distal region of the delivery catheter on the first, inner catheter shaft and a piece of the implant engages the eyelets or cut-outs, and wherein a distal portion of the second, outer catheter shaft is formed as an implant capsule for encasing the implant during the insertion process, the delivery catheter further comprising a flexible distal support element having a substantially truncated cone-shaped portion, which tapers in the proximal direction, which extends proximally from the implant connector and is attached, directly proximally of the implant connector, in a fixed position to the first, inner catheter shaft, and/or further comprising a flexible proximal support element fixed to move with the outer shaft, and having a substantially truncated cone-shaped portion, which tapers in the proximal direction, and extends to form a transition between the outer catheter shaft and the implant capsule.

2. The delivery catheter according to claim 1, wherein the proximal support element comprises a cylindrical distal portion having a diameter adapted to the inner diameter of the implant capsule and the outer diameter of the implant when crimped, the proximal support element further comprising a cylindrical proximal portion, of which the outer diameter is adapted to that of the first, inner catheter shaft, and a substantially truncated cone-shaped middle portion, which forms a continuous transition between the distal and proximal cylindrical portion.

3. The delivery catheter according to claim 2, wherein the proximal support element comprises a multiplicity of incisions.

4. The delivery catheter according to claim 2, wherein the proximal support element is formed as an injection-moulded part or turned part.

5. The delivery catheter according to claim 1, wherein the proximal support element is formed as an injection-moulded part or turned part.

6. The delivery catheter according to claim 1, wherein the proximal support element comprises a multiplicity of incisions.

7. The delivery catheter according to claim 6, wherein the incisions each extend tangentially over a part of the circumference of the proximal support element.

8. The delivery catheter according to claim 7, wherein the incisions each extend tangentially over a majority of the circumference of the support element.

9. The delivery catheter according to claim 1, wherein the distal support element comprises a distal end, of which the outer diameter is adapted to the inner diameter of the implant capsule and the outer diameter of the implant when crimped, and comprises a proximal end, of which the inner diameter is adapted to the outer diameter of the first, inner catheter.

10. The delivery catheter according to claim 1, wherein the distal support element is formed as a solid plastic part or stainless steel part with an inner lumen, of which the diameter is adapted to the outer diameter of the first, inner catheter shaft.

11. The delivery catheter according to claim 10, the distal support element comprises a multiplicity of incisions.

12. The delivery catheter according to claim 11, wherein the incisions extend tangentially over the circumference of the distal support element.

13. The delivery catheter according to claim 12, wherein the incisions extend over a majority of the circumference of the distal support element.

14. The delivery catheter according to claim 1, wherein the ratio between length and greatest diameter of the distal and/or proximal support element is between 2 and 7.

15. The delivery catheter according to claim 14, wherein the ratio between length and greatest diameter of the distal and/or proximal support element is between 3 and 5.

16. The delivery catheter according to claim 1, wherein the ratio between length and greatest diameter of the distal and/or proximal support element is between 3.5 and 4.5.

17. The delivery catheter according to claim 1, wherein the ratio between the length of the distal and/or the proximal support element and the length of the implant capsule is between 0.13 and 0.82.

18. The delivery catheter according to claim 17, wherein the ratio between the length of the distal and/or the proximal support element and the length of the implant capsule is between 0.28 and 0.42.

19. The delivery catheter according to claim 1, wherein the implant comprises a prosthetic heart valve.

20. The delivery catheter according to claim 1, wherein the proximal support element is formed as a hollow body, such that the distal support element at least partially fits within the proximal support element.

21. The delivery catheter according to claim 20, wherein the cone-shaped portions of the proximal and distal support elements exhibit different radii.

22. The delivery catheter according to claim 20, wherein the cone-shaped portions of the proximal and distal support elements comprise a stop.

23. The delivery catheter according to claim 20, wherein the cone-shaped portions of the proximal and distal support elements are structured to avoid any wedging of the implant.

24. A delivery catheter for implanting a self-expanding implant, the delivery catheter comprising a first, inner catheter shaft arranged inside at least one second, outer catheter shaft, wherein the implant is arranged in the distal region of the delivery catheter on the first, inner catheter shaft, and wherein a distal portion of the second, outer catheter shaft is formed as an implant capsule for encasing the implant during the insertion process, the delivery catheter further comprising a flexible distal support element having a substantially truncated cone-shaped portion, which tapers in the proximal direction, which is attached, directly proximally of an implant connector, in a fixed position to the first, inner catheter shaft and further comprising a flexible proximal support element fixed to move with the outer catheter shaft, and having a substantially truncated cone-shaped portion, which tapers in the proximal direction, and extends to form a transition between the outer catheter shaft and the implant capsule, wherein the distal and the proximal support element together support a proportion of the length of the implant capsule of at least 0.25 to 0.85 for preventing kink formation of the implant capsule or outer catheter shaft.

25. The delivery catheter according to claim 24, wherein the distal and the proximal support element together support a proportion of the length of the implant capsule of at least 0.45 to 0.65.

26. A delivery catheter for implanting a self-expanding implant, the delivery catheter comprising an inner shaft, an outer shaft around the inner shaft, an implant capsule of widened diameter at a distal end of the outer shaft and fixed with respect to the rest of the outer shaft, an implant connector within the implant capsule, the implant connector being fixed with respect to the inner shaft, an implant in the implant capsule and engaged to the implant connector, a flexible distal support fixed directly proximally of the implant connector to move with the inner shaft and having a substantially truncated cone-shaped portion that tapers and extends proximally from the implant connector, and a flexible proximal support having a substantially truncated cone-shaped portion fixed to move with the outer shaft and having a taper extending proximally, the flexible proximal support extending to form a transition between the outer shaft and the implant capsule.

\* \* \* \* \*